United States Patent
Thomson et al.

(10) Patent No.: US 6,856,668 B1
(45) Date of Patent: Feb. 15, 2005

(54) METHOD OF TREATING A TUMOR BY PRE-IRRADIATION

(75) Inventors: Euan Thomson, Harvard, MA (US); Mark Dinsmore, Sudbury, MA (US)

(73) Assignee: Carl Zeiss AG, Oberkochen (DE)

( * ) Notice: Subject to any disclaimer, the term of this patent is extended or adjusted under 35 U.S.C. 154(b) by 104 days.

(21) Appl. No.: 10/133,079

(22) Filed: Apr. 26, 2002

Related U.S. Application Data

(60) Provisional application No. 60/351,801, filed on Jan. 25, 2002.

(51) Int. Cl.[7] .................................................. A61N 5/10
(52) U.S. Cl. ............................. 378/65; 378/64; 604/20
(58) Field of Search ........................... 378/64, 65, 119; 600/3, 427; 604/20, 21

(56) References Cited

U.S. PATENT DOCUMENTS

| | | | |
|---|---|---|---|
| 5,153,900 A | 10/1992 | Nomikos et al. ............. 378/65 |
| 5,369,679 A | 11/1994 | Sliski et al. ................... 378/65 |
| 5,422,926 A | 6/1995 | Smith et al. ................. 378/121 |
| 5,428,658 A | * 6/1995 | Oettinger et al. ........... 378/119 |
| 5,452,720 A | * 9/1995 | Smith et al. ................ 600/427 |
| 5,818,902 A | * 10/1998 | Yu ............................... 378/65 |
| 6,480,568 B1 | 11/2002 | Dinsmore ..................... 378/65 |
| 6,556,651 B1 | * 4/2003 | Thomson et al. ............. 378/65 |

* cited by examiner

Primary Examiner—David V. Bruce
Assistant Examiner—Courtney Thomas
(74) Attorney, Agent, or Firm—McDermott Will & Emery LLP

(57) ABSTRACT

A method is provided for treating a tumor by pre-irradiation. The location, size, and shape of the tumor is identified. A region that includes the tumor as well as a surrounding portion most likely to contain residual tumorous cells is identified. The identified region is irradiated with therapeutic radiation, such as x-rays, prior to surgical removal of the tumor. The tumor is removed after irradiation of the identified region, leaving only the pre-irradiated surrounding portion. The risk of recurrence of tumorous growth after resection of the tumor may be significantly reduced.

18 Claims, 4 Drawing Sheets

METHOD OF TREATING A TUMOR BY PRE-IRRADIATION

CROSS-REFERENCE TO RELATED APPLICATIONS

This application claims benefit of U.S. Provisional Application Ser. No. 60/351,801, entitled "Array of Miniature Radiation Sources" and filed on Jan. 25, 2002.

STATEMENT REGARDING FEDERALLY SPONSORED RESEARCH

Not Applicable

REFERENCE TO MICROFICHE APPENDIX

Not Applicable

BACKGROUND

In the field of medicine, radiation may be used for diagnostic, therapeutic and palliative purposes. Therapeutic use of radiation such as x-rays and y-rays typically involves using these rays to eradicate malignant cells. Conventional radiation treatment systems used for medical treatment, such as the linear accelerators that produce high-energy x-rays, utilize a remote radiation source external to the targeted tissue. A beam of radiation is directed at the target area, for example a malignant tumor inside the body of a patient. The x-rays penetrate the patient's body tissue and deliver x-ray radiation to the cancer cells, usually seated deep inside the body. This type of treatment is referred to as teletherapy because the radiation source is located at some distance from the target. This treatment suffers from the disadvantage that tissue disposed between the radiation source and the target is exposed to radiation. To reach the cancer cells, the x-rays from an external radiation source must usually penetrate through normal surrounding tissues. Non-cancerous tissues and organs are thus also damaged by the penetrating x-ray radiation.

Brachytherapy, on the other hand, is a form of treatment in which the source of radiation is located close to, or in some cases within, the area receiving treatment. Brachytherapy, a word derived from the ancient Greek word for close ("brachy"), offers a significant advantage over teletherapy, because the radiation is applied primarily to treat only a predefined tissue volume, without significantly affecting the tissue adjacent to the treated volume. The term brachytherapy is commonly used to describe the use of "seeds," i.e. encapsulated radioactive isotopes which can be placed directly within or adjacent the target tissue to be treated. Handling and disposal of such radioisotopes, however, may impose considerable hazards to both the handling personnel and the environment.

The term "x-ray brachytherapy" is defined for purposes of this application as x-ray radiation treatment in which the x-ray source is located close to or within the area receiving treatment. An x-ray brachytherapy system, which utilizes a miniaturized low power radiation source that can be inserted into, and activated from within, a patient's body is disclosed in U.S. Pat. No. 5,153,900 issued to Nomikos et al. (the "'900 patent"), U.S. Pat. No. 5,369,679 to Sliski et al. (the "'679 patent"), U.S. Pat. No. 5,422,926 to Smith et al. (the "'926 patent"), and U.S. Pat. No. 5,428,658 to Oettinger et al. (the "'658 patent"), all owned by the assignee of the present application, all of which are hereby incorporated by reference. The x-ray brachytherapy systems disclosed in the above-referenced patents include miniaturized, insertable x-ray probes that are capable of controllably producing and delivering low power x-ray radiation, while positioned within or in proximity to a predetermined region to be irradiated. In this way, x-ray radiation need not pass through the patient's skin, bone, or other tissue prior to reaching the target tissue. The probe may be fully or partially implanted into, or surface-mounted onto a desired area, within a treatment region of a patient. The insertable probe emits low power x-rays from a nominal, or effective "point" source located within or adjacent to the desired region to be irradiated, so that substantially only the desired region is irradiated, while irradiation of other regions are minimized. X-ray brachytherapy offers the advantages of brachytherapy, while avoiding the use and handling of radioisotopes. Also, x-ray brachytherapy allows the operator to control over time the dosage of the delivered x-ray radiation.

In oncology, x-ray brachytherapy treatment generally involves positioning the insertable x-ray probe into or adjacent to the tumor so as to deliver therapeutic radiation to the tumor. Alternatively, the x-ray probe may be inserted into a post-operative site, i.e. into the site where the tumor or a portion of the tumor was removed, so as to treat the tissue adjacent the site with a local boost of radiation. A serious problem in the treatment of cancerous tumors is the recurrence of tumorous growth after surgery. Frequently, even after surgical removal of a tumor, there is a high risk of recurrence of tumorous growth in the region surrounding the resected tumor. Many patients with recurrent tumors suffer tumor progression, i.e. metastasis. Such recurrent tumorous growth is due to the spread to tumorous cells around the operative site.

It is therefore desirable to reduce the risk of recurrent tumorous growth near or around the operative site, while at the same time preventing radiation damage to non-cancerous tissue.

SUMMARY

The present invention provides a method for treating a tumor by pre-irradiation of the tumor and a surrounding region. The method includes identifying the location, size, and shape of the tumor. Techniques such as computed tomography (CT) and magnetic resonance imaging (MRI) may be used. Once the location of the tumor has been determined, a region that surrounds the tumor and that is most likely to contain residual tumorous cells is identified, while the tumor is still in place. This region includes the tumor, and a surrounding portion. This region is irradiated with therapeutic radiation, such as x-rays. Preferably, the therapeutic radiation is directed to one or more targeted areas within the region. These targeted areas are determined in accordance with a pre-planned irradiation profile. In a preferred embodiment, x-ray brachytherapy systems are used to deliver therapeutic x-rays to the identified region.

The tumor is surgically removed, subsequent to the irradiation step. Only the pre-irradiated surrounding portion remains within the identified region. Because the region surrounding the tumor and most likely to contain residual tumorous cells has been irradiated prior to surgery, the risk of recurrence of tumorous growth may be substantially reduced.

DETAILED DESCRIPTION

In the present invention, a method of treating tumors is presented, in which the tumor as well as the region surrounding the tumor and most likely to contain residual cancerous cells, are irradiated prior to surgical removal of the tumor. Because the radiation treatment is planned and delivered whilst the tumor is still in place, rather than after surgical removal of the tumor, the tissue that is most at risk of recurrence or metastasis can be identified. In the present invention, an x-ray brachytherapy system is used, which permits controllable delivery of x-ray radiation while positioned within or near a targeted region, so as to minimize damage to non-targeted tissue. By irradiating a tumor and the surrounding region before, rather than after surgical removal of the tumor, the method of the present invention may reduce the risk of recurrence of the tumor due to the spreading of tumor cells around the operative site.

Figure 1:
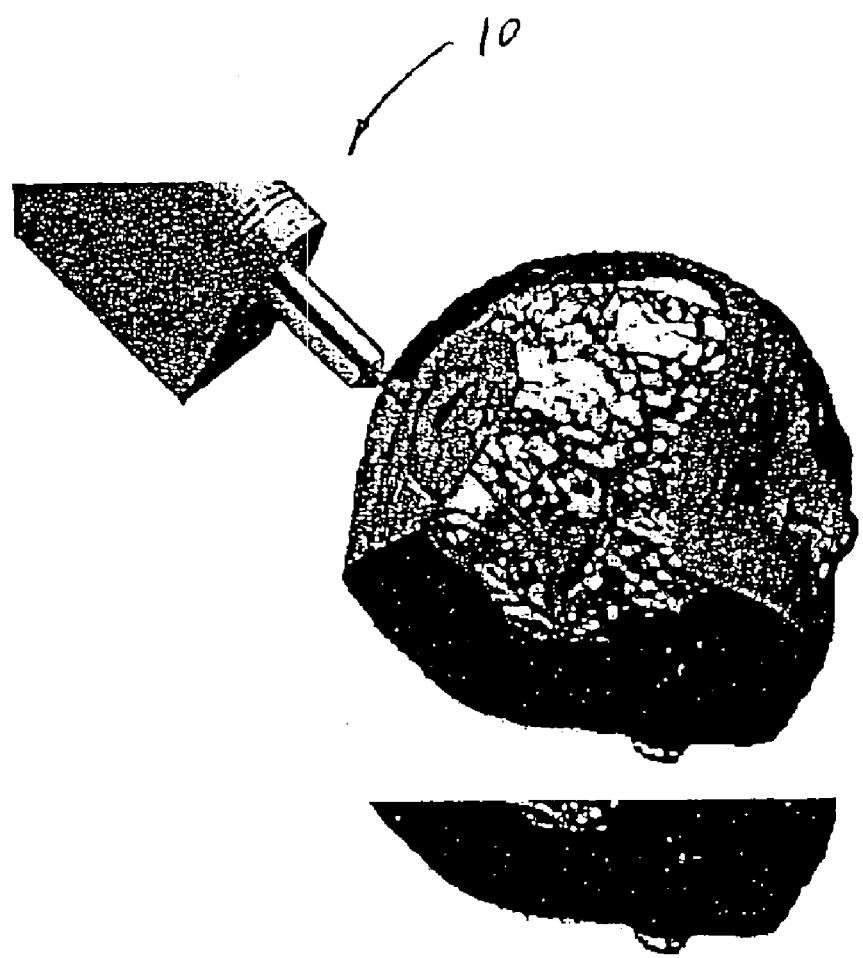
FIG. 1 schematically illustrates the delivery of an intra-operative dose of therapeutic radiation to a region surrounding a resected tumor in the brain, in accordance with one embodiment of the present invention.

FIG. 1 presents a schematic, overall view of a method of delivering an intraoperative dose of therapeutic radiation to a tumor in the brain and the region surrounding the tumor, as performed in accordance with one embodiment of the present invention. While a brain tumor is shown as being treated, the method of the present invention is applicable to any kind of tumors located at any anatomical area. Because brain tumors lack substantial regenerative ability, the treatment of brain tumors requires precise techniques to bring about specific tissue destruction.

In overview, the method of the present invention includes identifying the location of a tumor within the patient's anatomy. The region that surrounds the tumor and that is most likely to contain residual cancerous cells is then identified. The identified region thus includes the tumor, and a surrounding portion. An x-ray brachytherapy system 10, as disclosed for example in the '900 patent, the '679 patent, the '926 patent, and the '658 patent, is used to irradiate the tumor and the surrounding portion with x-rays, prior to surgical removal of the tumor. The tumor is then removed, leaving only the irradiated surrounding portion.

Figure 2A:
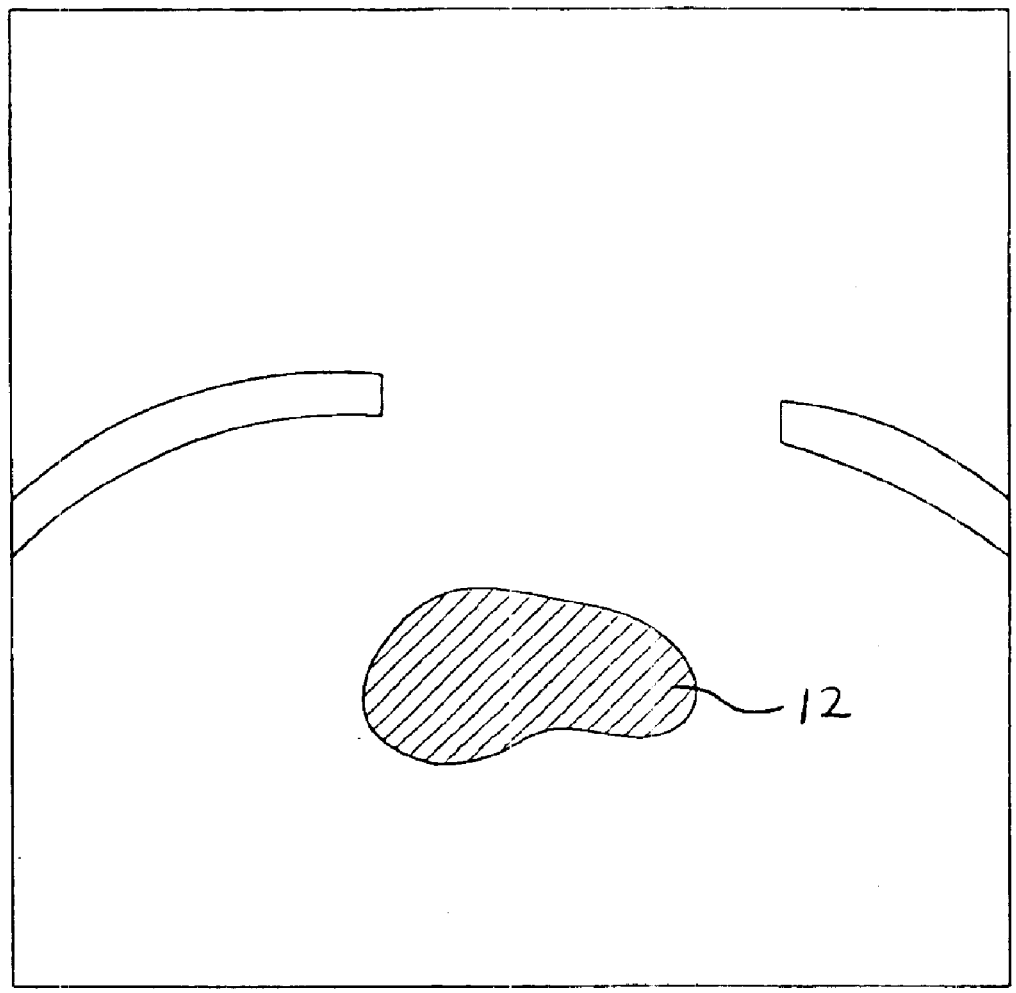
FIG. 2(a) schematically illustrates the step of assessing the location, size, and shape of a tumor.

The initial step in implementing a treatment method in accordance with the present invention, namely identifying the location, size, and shape of a tumor 12 in a patient, is schematically illustrated in FIG. 2(a). Typically, malignant cells are identified and located using techniques generally available in the art, such as computerized tomography (CT) scanning, or magnetic resonance imaging (MRI. A needle-type biopsy of the tumor may be performed, to confirm the diagnosis. The size and shape of the tumor 12 must be defined, and the location of the tumor within the patient's body must be precisely determined. It may be necessary to identify radiation-sensitive critical biological structures surrounding the tumor 12. For tumors having complex geometries or close-by critical structures, computer-based 3-D (three-dimensional) imagery may be used to identify the size, shape, and location of the tumors. In this case, tumors and critical structures may be segmented on a series of digitized CT scans, and a 3-D composite is rendered, which allows viewing of the tumor from any direction.

Figure 2B:
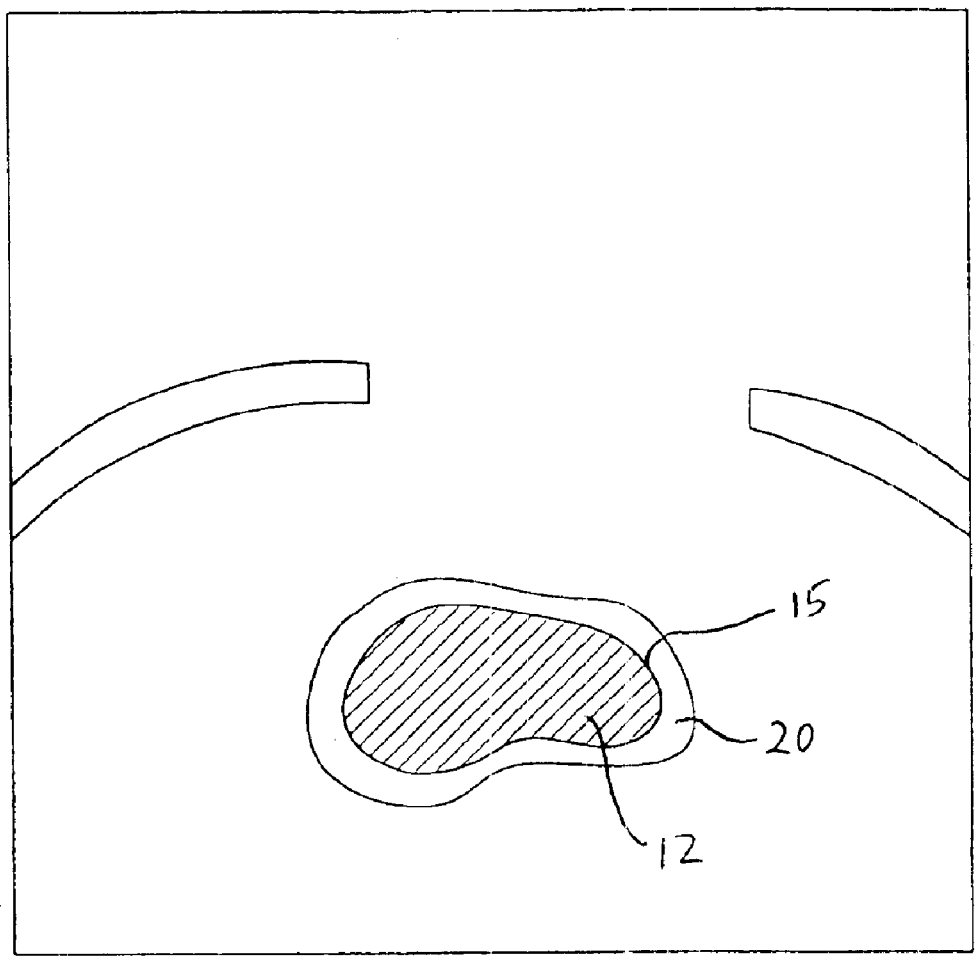
FIG. 2(b) schematically illustrates the step of assessing a region that surrounds the tumor and that is most likely to contain residual tumorous cells.

Once the location, size, and shape of the tumor 12 has been assessed with sufficient precision, a region 20 that surrounds the tumor, and that is most likely to contain residual tumorous cells, is identified. This step is illustrated in FIG. 2(b), and involves selecting the region 20 to be treated, and the appropriate radiation dosage. The region 20 comprises the tumor 12, and a surrounding portion 15. Typically, the surrounding portion 15 includes residual cancerous cells. Because the radiation treatment is planned and delivered whilst the tumor is still in place, rather than after surgical removal of the tumor, the tissue that is most at risk from recurrence can be identified, using diagnostic and pathological techniques known in the art.

The tumor 12 as well as the surrounding portion 15 of the identified region 10 are irradiated with therapeutic radiation, such as x-rays. While x-rays are used in a preferred embodiment of the present invention, treatments that use other forms of therapeutic radiation, for example y-rays, are also within the scope of the present invention. In one embodiment, an array of radioactive radiation sources may be used for delivering therapeutic radiation to the region 10.

Figure 3:
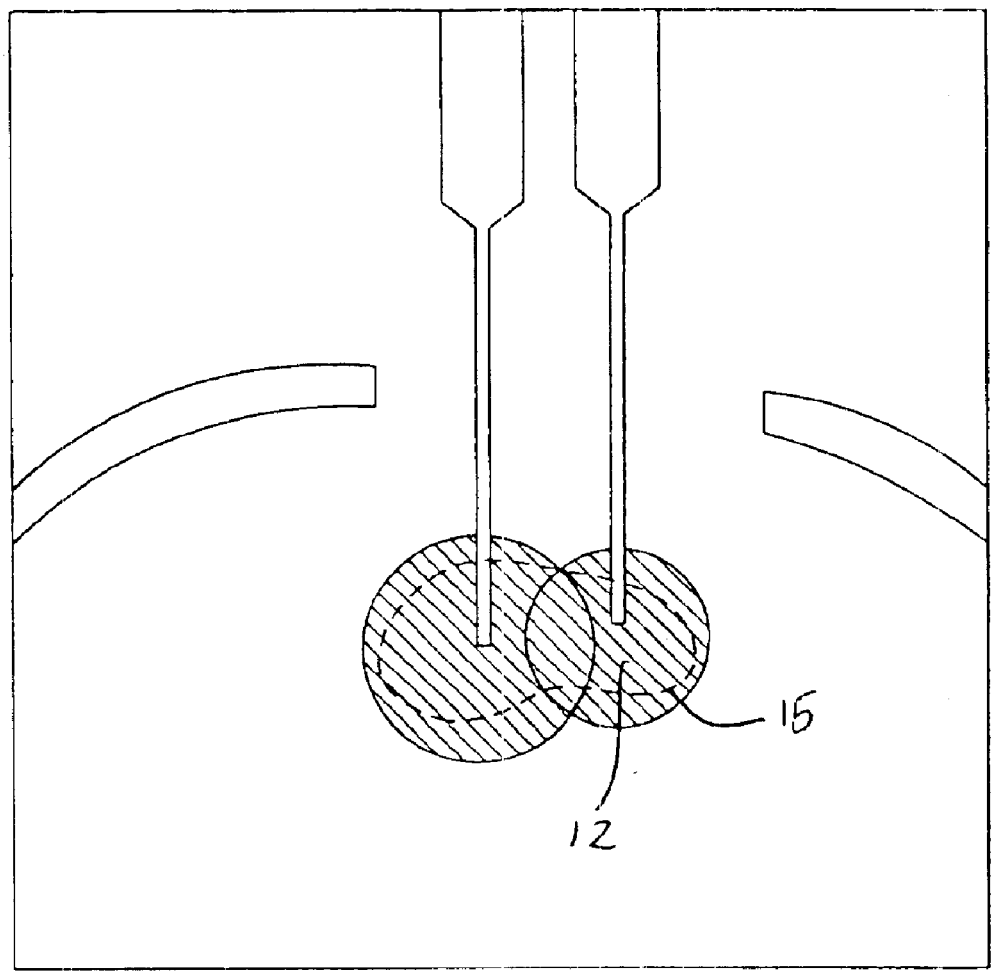
FIG. 3 schematically illustrates the step of irradiating the tumor and the surrounding region with therapeutic radiation, at targeted areas.

FIG. 3 illustrates the step of irradiating the tumor 12 and the surrounding portion 15 within the region 20, with therapeutic radiation. Rather than irradiating tissue surrounding a resected tumor after surgical removal of the tumor, the method of the present invention features delivering one or more intense, "boost" dose of therapeutic radiation to the region 15 surrounding the identified tumor 12. In one form of the invention, the delivery of therapeutic radiation takes place within a single application session, typically not lasting more than one month.

Radiation treatment planning for the region 20 may involve determining isodose contours, where the term isodose contour as used herein refers to a surface of a three-dimensional volume on which every point experiences the same x-ray absorption per unit mass of tissue. Such isodose contours, determined for example after examining the 3-D imaging results, may overlaid over the tumor, and a desired irradiation profile may be mapped out for the region 20. In this way, tumor 12 itself may be used as a "sacrificial" tissue, in order to achieve a uniform dose of radiation in the target tissue. The therapeutic x-rays may be specifically directed to one or more targeted areas within the region 10, where the targeted areas are determined in accordance with a predetermined irradiation profile established during radiation treatment planning.

In a preferred embodiment of the invention, an x-ray brachytherapy system 10 is used to deliver therapeutic radiation to a tumor 12 in the brain. X-ray brachytherapy systems, such as the system 10, are adapted to controllably deliver low power x-ray radiation to desired target region. For example, devices such as the one generally disclosed in the '900 patent may be used, which includes a housing, and a hollow, tubular probe or catheter extending from the housing along an axis and having an x-ray emitting target at its distal end. The probe may enclose an electron source, such as a thermionic cathode. A more detailed description of the miniaturized x-ray probe is provided in the '900 patent.

Another form of an x-ray brachytherapy device, as disclosed in the '658 patent, may also be used. The system disclosed in the '658 patent includes an x-ray source disposed at the end of a flexible probe, such as a flexible fiber optic cable enclosed within a metallic sheath. In such a flexible probe, the electron source may be a photocathode. In a photocathode configuration, a photoemissive substance is irradiated by a LED or a laser source, causing the generation of free electrons. Typically, the flexible fiber optic cable couples light from a laser source or a LED to the photocathode. Such a flexible probe configuration is particularly useful for applications in which it is necessary to maneuvre the x-ray source around critical structures, such as nerves and other structures in the brain. A more detailed description of the an x-ray source with a flexible probe is provided in the '658 patent.

Alternatively, an optically driven x-ray source may be used, as described in U.S. patent application Ser. No. 09/884,561, which has issued as U.S. Pat. No. 6,480,568 (hereinafter the "'561" application). It is possible to reduce the power requirements of miniaturized therapeutic radiation sources used in x-ray brachytherapy, by optically driving the thermionic cathodes in the electron sources, instead of ohmically heating the thermionic cathodes. The '561 application discloses an optically driven (for example, laser driven) x-ray source using a reduced-power, increased efficiency electron source, which generates electrons with minimal heat loss. The '561 application discloses the use of laser energy to heat an electron emissive surface of a thermionic emitter, instead of using an electric current to ohmically heat an electron emissive surface of a thermionic emitter. With the optically driven thermionic emitter, electrons can be produced in a quantity sufficient to produce the electron current necessary for generating therapeutic radiation at the target, while significantly reducing the requisite power requirements.

In another form of the invention, the x-ray brachytherapy system 10 may be an array formed of a plurality of independently controllable, miniaturized therapeutic radiation sources, as disclosed in U.S. patent application Ser. Nos. 10/133,103 (which has issued as U.S. Pat. No. 6,556,651) and 10/133,048, (filed on even date herewith and hereby incorporated by reference).

Irradiating the region 20 thus involves positioning a miniaturized x-ray source 10, as described above, within or proximate to the tumor, and activating the x-ray source 10. An electron source in the x-ray source 10 is activated, so that a beam of electrons is generated along a beam path. The x-ray source 10 includes a target element having at least one x-ray emissive material. The target element is positioned in the beam path. When an optically driven x-ray source is used, such as the device disclosed in the '561 application, the electron source is a laser-activated thermionic cathode. In this case, a laser is activated so as to generate a beam of light. The beam of laser light is directed to a proximate end of a fiber optic cable, so that the laser light is transmitted through the fiber optic cable, from the proximate end onto a distal end. The transmitted laser light impinges upon a surface of the thermionic cathode, so that the surface is heated to an electron emitting temperature. Electrons are thereby thermionically emitted from the heated surface of the cathode.

An accelerating voltage is provided between the electron source and the target element so as to accelerate the electrons (generated by the electron source) toward the target element. Preferably, the accelerating voltage is provided by a high voltage power supply, as described in the '900 patent or the '658 patent. In a preferred embodiment, the electrons are accelerated to energies in the approximate range of 10 keV to 90 keV. The accelerated electrons strike the x-ray target element, so as to generate x-rays.

In the tumor resection step, the tumor 12 is surgically removed from the region 20, so that only the pre-irradiated surrounding portion 15 remains within the region 20. The step of irradiating the surrounding portion 15 precedes in time the step of removing the tumor 12, unlike conventional procedures in which post-operative tumor resection sites are given preventive "boosts" of therapeutic radiation.

The method of the present invention provides many advantages, compared to such conventional procedures. A major advantage is that the method may significantly reduce the widespread risk of recurrence of tumorous growth, caused by the spread of tumor cells around the operative site. Another advantage is that the oncological treatment can be planned and delivered while the tumor is still in place, enabling tissue to be identified that is most at risk for recurrence. Once a tumor has been removed, such identification is more difficult. Yet another advantage is that by destroying cancerous cells before surgically removing the tumor, the method of the present invention avoids leaving behind residual cancerous cells in situ, during the surgical removal process. In addition, in the present invention the tumor may be used as a "sacrificial" tissue, so as to achieve the delivery of a uniform dose of radiation to target tissue. Finally, in the present invention the radiation dose to tissue other than tissue immediately surrounding the tumor can be minimized, enabling follow-up radiation therapy as required.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for treating a tumor, comprising:
   a) identifying a location of the tumor;
   b) identifying a region comprising the tumor and a surrounding portion;
   c) irradiating said region, including said tumor and said surrounding portion, with a therapeutically effective amount of radiation; and
   d) surgically removing at least a portion of said tumor, subsequent to said irradiation.

2. A method according to claim 1, wherein the step of irradiating said region with therapeutic radiation comprises the step of irradiating said region with x-rays.

3. A method according to claim 1, wherein said surrounding portion comprises at least one residual cancerous cell.

4. A method according to claim 1, wherein the step of identifying a location of the tumor further comprises the steps of identifying a size and a shape of the tumor.

5. A method according to claim 1, wherein said therapeutic radiation comprises radiation generated by a radioactive source.

6. A method according to claim 1, wherein the step of irradiating said region with therapeutic radiation lasts for no more than one application session.

7. A method according to claim 6, wherein said application session lasts less than one month.

8. A method according to claim 1, wherein the step of identifying a location of the tumor is performed using at least one of computed tomography (CT) and magnetic resonance imaging (MRI).

9. A method according to claim 1, wherein the step of identifying the region surrounding the tumor comprises the step of assessing an area within said region most likely to contain one or more residual tumorous cells.

10. A method according to claim 1, wherein the step of irradiating said region comprises the step of irradiating said tumor and said surrounding portion at one or more targeted areas within said region.

11. A method according to claim 10, wherein said targeted areas are determined in accordance with a predetermined irradiation profile.

12. A method according to claim 1, wherein the step of irradiating said region comprises the steps of:
   a) positioning a miniaturized x-ray source proximate to the tumor; and
   b) activating the x-ray source.

13. A method according to claim 1, wherein the step of irradiating said region comprises the steps of:
   a) positioning an array of therapeutic radiation sources proximate to said region; and b) activating at least one of said therapeutic radiation sources.

14. A method according to claim 1, wherein the step of irradiating said region comprises the steps of:
   a) positioning at least one miniaturized x-ray source proximate to the tumor, wherein said x ray source comprises an electron source, and a target element including at least one x-ray emissive material;
   b) activating said electron source so as to generate a beam of electrons along a beam path;
   c) providing an accelerating voltage between each electron source and said target element so as to accelerate said beam of electrons toward said target element; and
   d) causing the beam of electrons to strike the target element so as to generate x-rays.

15. A method according to claim 14, wherein said electron source comprises a thermionic cathode, and wherein the step of activating said electron source so as to generate a beam of electrons includes the steps of:
   i) activating a laser so as to generate a beam of light;
   ii) directing the beam of light to a proximate end of a fiber optic cable so as to transmit the beam of light through the fiber optic cable onto a distal end of the fiber optic cable;
   iii) causing the transmitted beam of light to impinge upon a surface of the thermionic cathode, thereby heating at least a portion of the surface to an electron emitting temperature so as to cause thermionic emission of electrons from said surface.

16. A method according to claim 14, wherein the step of providing an accelerating voltage between said electron source and said target element includes the step of activating a high voltage power supply so as to accelerate said electrons to energies in the approximate range of 10 keV to 90 keV.

17. A method according to claim 1, wherein the step of irradiating said region with therapeutic radiation includes the step of using a flexible probe to thread an x-ray source down a bodily passageway.

18. A method according to claim 1, wherein the step of irradiating said region precedes in time the step of removing said tumor.

* * * * *